United States Patent
Premachandran et al.

(10) Patent No.: US 7,616,987 B2
(45) Date of Patent: Nov. 10, 2009

(54) MICROPROBE FOR 3D BIO-IMAGING, METHOD FOR FABRICATING THE SAME AND USE THEREOF

(75) Inventors: Chirayarikathuveedu Sankarapillai Premachandran, Singapore (SG); Janak Singh, Singapore (SG); Joseph Suresh Paul, Coehin (IN); Pamidighantam Venkata Ramana, Singapore (SG); Colin James Richard Sheppard, Singapore (SG)

(73) Assignees: Agency For Science, Technology and Research, Centros (SG); National University of Singapore, Singapore (SG)

( * ) Notice: Subject to any disclaimer, the term of this patent is extended or adjusted under 35 U.S.C. 154(b) by 271 days.

(21) Appl. No.: 11/244,919

(22) Filed: Oct. 5, 2005

(65) Prior Publication Data
US 2006/0195019 A1    Aug. 31, 2006

Related U.S. Application Data (60) Provisional application No. 60/615,926, filed on Oct. 5, 2004.

(51) Int. Cl.
*A61B 6/00* (2006.01)
(52) U.S. Cl. .................................. 600/476; 600/473
(58) Field of Classification Search ................. 600/476, 600/167, 160, 473, 300; 385/119; 356/123, 356/445
See application file for complete search history.

(56) References Cited

U.S. PATENT DOCUMENTS

| | | | |
|---|---|---|---|
| 6,386,716 B2 | 5/2002 | Hagelin et al. | 359/871 |
| 6,480,320 B2 | 11/2002 | Nasiri | 359/291 |
| 6,485,413 B1 * | 11/2002 | Boppart et al. | 600/160 |
| 6,504,643 B1 | 1/2003 | Peeters et al. | 359/290 |
| 6,528,780 B1 * | 3/2003 | Mitsuoka et al. | 250/216 |
| 6,556,737 B1 | 4/2003 | Miu et al. | 385/16 |
| 6,563,106 B1 | 5/2003 | Bowers et al. | 250/216 |
| 2004/0076390 A1 * | 4/2004 | Dong Yang et al. | 385/116 |
| 2005/0136663 A1 * | 6/2005 | Gan et al. | 438/689 |

FOREIGN PATENT DOCUMENTS

WO    WO 03/050590    6/2003

OTHER PUBLICATIONS

Rector et al., Journal of Neuroscience Methods, 91 (1999) 135-145.
Salsberg BM et al., J Gen Physiol 1985; 86:395-411.
Tasaki et al., Biochem Biophys Res Commun 1992; 188(2):559-561.

* cited by examiner

*Primary Examiner*—Eric F Winakur
*Assistant Examiner*—Katherine L Fernandez
(74) *Attorney, Agent, or Firm*—K. David Crockett, Esq.; Crockett & Crockett (57) ABSTRACT

A microprobe that is capable of using an incident and reflected radiation ray for three-dimensional (3-D) bio-imaging. The microprobe comprises a hollow body closed at one end and having an aperture at an opposite end, at least one 3-D free space micromirror, at least one focusing lens, and a beam director or a beam coupler or other kind of device for beam coupling or splitting. The beam director is arranged at the aperture end of the hollow body and is adapted to direct the incident ray into the hollow body via the aperture. Within said hollow body is the at least one focusing lens and the at least one micromirror arranged respectively from the aperture, such that the distance between the focusing lens and the micromirror allows for the incident light ray to be directed onto the micromirror.

13 Claims, 12 Drawing Sheets

MICROPROBE FOR 3D BIO-IMAGING, METHOD FOR FABRICATING THE SAME AND USE THEREOF

This application claims priority to U.S. Provisional Application No. 60/615,926, filed Oct. 5, 2004.

FIELD OF THE INVENTION

The present invention relates to a device for three-dimensional (3-D) bio-imaging. The present invention also relates to a system for 3-D bio-imaging, the method of production of such a device and to the use of such a 3-D bio-imaging device and system in the analysis of a biological sample.

BACKGROUND OF THE INVENTION

When applying minimally invasive techniques in diagnosis and intervention, relying on 2D imaging comes with the disadvantage of a lack of depth perception. The performance and safety of delicate dissection or suturing during minimally invasive procedures may suffer when using 2D imaging, because a surgeon has to rely on motion parallax and other indirect evidence of depth. Where this is not sufficient, he needs to touch the tissues, in order to gauge depth, thereby significantly reducing the speed and precision at which minimally invasive surgical procedures can be performed.

For this reason there have been tremendous efforts of converting 2D data into reconstructed 3D impressions. Angiography, ultrasound, computer tomography, and magnetic resonance imaging are typical examples, where significant progress has been made in this field. Besides the risk of relying on software-generated images, these techniques often do not show real-time performance and lack the precision required for areas such as neurosurgery.

Reflected light images from neural structures disclose several correlates of neural activity (Rector et al., *Journal of Neuroscience Methods* 91 (1999) 135-145). Depending on the illumination wavelength used, indications of hemodynamic changes (e.g. 560 nm), metabolic protein conformational changes (<400 nm), or neuronal swelling (>600 nm) can serve as measures of local neural activity. Light reflectance techniques typically illuminate the brain surface with monochromatic light, and then detect back-scattered light from the tissue using a charged-coupled device (CCD) camera. Changes in the amount of back-scattered light are calculated as differences or ratios across time on a pixel-by-pixel basis, thereby forming a parametric map of light scattering or absorption changes within the tissue of interest. Such procedures for recording from large neural populations provide insight into neural interactions and neural network properties. The need to study many neurons simultaneously has driven significant advances in optical measurements of neural activation.

Most imaging studies using intrinsic optical signals have employed slow scan imaging technologies and steady-state stimulation to visualize hemodynamic changes associated with neural activation. Although some components of the hemodynamic signals are comparatively fast (<1 s), long integrated signal acquisition is used to average over fluctuations associated with the cardiac cycle. Subtraction techniques isolate those signals associated specifically with neural activity, and tend to eliminate vessel artifacts.

Attempts to image dynamic processes require more sophisticated characterization of optical changes associated with the cardiac cycle. In addition, a number of in vitro studies have identified fast light scattering changes associated with neural swelling during activation that parallel electrical events (Salzberg B M et al., *J Gen Physiol* 1985; 86:395-411 and Tasaki et al., *Biochem Biophys Res Commun* 1992; 188(2): 559-564). In order to image such changes in vivo, it is necessary to achieve high sensitivity, high time resolution, and to adequately account for the dynamics of other ongoing physiological processes that affect the overall optical signal. These include movement and spectral changes associated with the cardiac cycle.

Contact of the image probe with the tissue surface can serve as a mechanism for minimizing movement artifacts associated with the cardiac and respiratory cycles. Such contact stabilizes the tissue relative to the probe surface, and reduces pulsations typically seen in these preparations. For chronic studies, the bone is subsequently sealed around the probe using bone wax and dental acrylic allowing restoration of CSF pressure and further stabilizing the brain tissue through hydrostatic forces. Another mechanism for minimizing movement artifact involves an opening in the skull, which is then sealed with a glass window and filled with oil. Such methods minimize brain movement through the establishment of CSF pressure related hydrostatic forces; however, movements in neighboring brain regions (or a nearby vessel) may introduce movements through hydraulic effects. Additionally, use of an oil filled chamber precludes dark-field techniques, and specula reflectance becomes a major issue in the scattered light signals.

Previously in vivo optical techniques using coherent fiber optic image conduit have a focal plane limited to the tissue surface in contact with the probe. Such procedures generally form good images of the tissue surface. Also, since illumination surrounds the imaged area, dark-field methods eliminate specula reflectance from the tissue surface, and provide scattering information from deeper tissue (Rector et al, supra). Unfortunately, light from deeper structures is out of focus and the image is blurred. Because cells of interest are frequently located several hundred microns below the surface, it is desirable to focus below the surface to accurately measure deep structures. Optical techniques with deep focus capabilities would be especially useful for brain structures, which are otherwise difficult to access.

PCT patent application WO 03/050590 A1 describes an endoscopic imaging system. The endoscopic system uses a commercially available endoscopic sheath and uses a micro-electro-mechanical (MEM) micromirror to direct the incoming light beam to the lens and onto the sample area of interest. The scanning area of the system is forward-looking and directly ahead of the lens of the endoscope.

However, there remains a need for an imaging device capable of 3-D bio-imaging using minimally invasive techniques for use in dental applications, orthopedic surgery applications and for cancer diagnostic applications such as in providing an optical biopsy, for example. In addition, there is a need for an imaging system capable of focusing below the surface of the tissue to scan deep structures such as neurological structures, for example.

SUMMARY OF THE INVENTION

In one aspect, the invention provides a microprobe that is capable of using an incident and reflected radiation ray for three-dimensional (3-D) bio-imaging. The microprobe includes a hollow body, closed at one end, and having an aperture at an opposite end, at least one 3-D free space micromirror, at least one focusing lens, and a beam director. The beam director is arranged at the aperture end of the hollow body and is adapted to direct the incident ray into the hollow body via the aperture. Within the hollow body is the at least one focusing lens and the at least one micromirror arranged respectively from the aperture, such that the distance between the focusing lens and the micromirror allows for the incident light ray to be directed onto the micromirror.

In a further aspect, the invention provides a microprobe that is capable of using an incident and reflected light ray for three-dimensional (3-D) bio-imaging. The microprobe includes a hollow body closed at one end and having an aperture at an opposite end, at least one 3-D free space micromirror, at least one GRIN lens, at least one focusing lens, and a beam director. The beam director is arranged at the aperture end of the hollow body and is adapted to direct the incident light ray into the hollow body via the aperture. Within said hollow body are the at least one focusing lens, GRIN lens and micromirror arranged respectively from the aperture, such that the distance between the focusing lens, GRIN lens and the micromirror allows for the incident light ray to be directed onto the micromirror.

In yet another aspect, the invention provides a system for three-dimensional (3-D) bio-imaging having a microprobe, a radiation source optically coupled to the microprobe, and an image processing and visualization device, optically coupled to the microprobe such that the ray reflected by the micromirror is directed, via the aperture, to the image processing and visualization device by the focusing lens and beam director respectively.

In still another aspect, the invention provides a method of fabricating a microprobe that is capable of using an incident and reflected light ray for three-dimensional (3-D) bio-imaging, said method comprising:
(a) Providing a first substrate (Silicon, glass or any transparent material permeates rays having a wavelength between the visible spectrum to the far IR spectrum).
(b) Micro machining grooves on the surface of the first substrate for at least one focusing lens and at least one 3-D free space micromirror.
(c) Affixing the at least one focusing lens and micromirror in the respective grooves of the first substrate.
(d) Providing a second substrate.
(e) Micro machining an aperture and corresponding grooves on the surface of the second substrate to accommodate the affixed at least one focusing lens and a 3-D free space micromirror.
(f) Bonding the first and second substrates together to form the microprobe such that a hollow body closed at one end and having the aperture at an opposite end is enclosed within the first and second substrate.

In another aspect, the invention provides a method of creating a three-dimensional (3-D) image of a biological sample, said method comprising:
(a) Inserting a microprobe into a biological sample to be analyzed,
(b) Providing a radiation source, which is capable of emitting a radiation ray,
(c) Introducing the radiation ray emitted by the radiation source into the probe, and
(d) Processing the outgoing ray to generate an image.

These and other features of the invention will be better understood when read in view of the following drawings and detailed written description.

DETAILED DESCRIPTION OF THE INVENTION

One aspect of the invention relates to a microprobe that is capable of using an incident and reflected radiation ray for three-dimensional (3-D) bio-imaging. Such a microprobe includes a hollow body closed at one end and having an aperture at an opposite end, at least one 3-D free space micromirror, at least one focusing lens, and a beam director.

The beam director is arranged at the aperture end of the hollow body and is adapted to direct the incident ray into the hollow body via the aperture. Within the hollow body is the at least one focusing lens and the at least one micromirror. The focusing lens and the micromirror are arranged in the stated sequence (i.e. the focusing lens being nearer to the aperture) respectively from the aperture. The distance between the focusing lens and the micromirror within the hollow body is such that it allows for the focusing lens to direct the incident ray onto the micromirror.

In one exemplary embodiment, the positioning of the focusing lens may be such that said focusing lens directs the ray onto the micromirror and focuses the ray on the micromirror as well. In an alternative exemplary embodiment, the focusing lens may merely direct the ray onto the micromirror (perhaps partially focused), which in turn reflects the (partially) focused ray onto an area of interest. Accordingly, in this alternative exemplary embodiment, the positioning of the focusing lens with respect to the micromirror allows for the reflected ray to be focused at the specific area of interest as opposed to the earlier embodiment where the focus of the ray is at the micromirror.

In the microprobe, any type of focusing lens may be used to focus the incoming ray. Examples of such focusing lenses include, but are not limited to, a gradient index (GRIN) lens, a spherical or aspherical lens, a cylindrical lens, an achromatic lens, a convex lens and a concave lens, planoconvex/concave lens, a drum lens and a fluidic lens.

In another embodiment, the microprobe may include, apart from the focusing lens, an additional lens. This additional lens may be any suitable lens that further aids in the focusing of the ray. An example of such an embodiment may be the case when the additional lens is a GRIN lens. In this exemplary embodiment, the GRIN lens is arranged between the focusing lens and the micromirror. Again, as with all the embodiments disclosed herein, such an arrangement in the microprobe also allows for the incident ray to be directed onto the micromirror.

In the above-mentioned exemplary embodiment wherein the additional lens is a GRIN lens, the ray may be (partially) focused to be incident on the GRIN lens first. Due to the varying refractive properties of the GRIN lens, said GRIN lens may further focus the ray such that the focal point lies in the micromirror. Alternatively, the GRIN lens may only further (partially) focus the ray such that the reflected ray from the micromirror is focused at the specific area of interest.

In a further embodiment, the microprobe may include a plurality (two or more) of focusing lenses and a plurality (two or more) of micromirrors. The plurality of focusing lenses may be a mixture of the aforesaid lenses or may be of the same type of lens. Essentially, in the embodiment having a plurality of lenses and mirrors, the focusing lenses may be situated such that they direct the ray to the micromirrors such that the focal point either lies on the micromirror or is on the area of interest after being reflected by the micromirrors. In a further embodiment, the microprobe may further include a Radio Frequency (RF) unit. The RF unit may function as a transmitter, a receiver or a transceiver device.

The hollow body may be made from any suitable transparent material that is biocompatible or bioinert and allows for surface modification by micro machining, etching or electrical discharge machining (EDM) processes, for example. In one aspect, the hollow body is formed from at least two patterned substrates each of which may be made of same or different semiconducting materials such as Silicon (Si) or Gallium Arsenide (GaAs). Each of the two substrates can also be made from an electrically non-conductive material such as glass, or a polymeric material that is transparent to the radiation/light used. Examples of suitable polymeric materials used may be, but are not limited to, polymeric silicones, polycarbonates, or polyacrylic acid derivatives such as Plexiglas® to name only a few. Polymeric silicones may include silane polymers, silicone polymers, siloxane polymers, and inorganic silicon-nitrogen based polymers. Illustrative examples of polymeric silicone, which can be used in the substrate, are polydimethylsiloxane (PDMS), polydiethylsiloxane and polydipropylsiloxane. If a polymer-based material or glass is used to fabricate the substrate, a molding/casting method may be used.

The lateral surfaces of the substrates are patterned and when said substrates are bonded together, the lateral surfaces form the inner wall of the hollow body. Prior to bonding, the lateral surface (which later becomes the inner surface when bonded together with a corresponding substrate) includes grooves formed thereon.

The grooves on the inner surface of the hollow body are micro machined such that they become adapted to having the focusing lens, the GRIN lens, or any combination of lenses, and the micromirror affixed therein and arranged in the above-prescribed manner respectively from the aperture. The 3-D micromirror is affixed to the grooves by means of precision bonding. The detailed fabrication process of the microprobe will be discussed below.

Any type of 3-D free space micromirror such as, but not limited to, that which is disclosed in US Patent application 2005/0136663 A1 may be used. Alternative micromirrors that may also be used in conjunction with the microprobe include those described in U.S. Pat. Nos. 6,563,106, 6,556,737, 6,480,320, 6,504,643 and 6,386,716, for example. Accordingly, the entire contents of US Patent application 2005/0136663 and U.S. Pat. Nos. 6,563,106, 6,556,737, 6,480,320, 6,504,643 and 6,386,716 are incorporated by reference to the present specification.

In a microprobe that, for example, includes at least one 3-D free space micromirror, as described in 2005/0136663 A1, said 3-D free space micromirror includes at least one actuator, and at least one flexible spring connecting the crystal silicon actuator to the silicon micromirror. The various components of the 3-D free space mirror may be fabricated from Silicon (Si) or other micromachinable materials of different thicknesses for the different components of the device. A detailed description of the fabrication of the 3-D free space micromirror, and the materials utilized therein, is given in the US Patent application 2005/0136663. The actuation of the at least one crystal silicon actuator may be carried out by a means selected from the group consisting of thermal variation, electrostatic charging, piezoelectric transduction and magnetic excitation.

In an exemplary embodiment of the 3-D micromirror, said 3-D micromirror may be supported by four actuators made of silicon or other type of micromachinable material. Each actuator may be actuated vertically by the above-mentioned methods to achieve various angular positions. For example, varying the current or voltage through the actuators may carry out the actuation. Accordingly, the extent of the actuation (orientation), and corresponding ray deflection, will correlate to the increase or decrease of the current or voltage to the actuator.

The 3-D free space micromirror may also be adapted to direct and collect light rays in a plurality of planes. As the 3-D micromirror can direct an incoming ray in 3D free space, about 360 degrees about the central axis of the micro probe by means of tilting in angular orientations in an analogue manner, the micromirror is capable of directing rays to specific areas of interest surrounding the entire circumferential portion of the microprobe. Accordingly, in one embodiment, the 3-D free space micromirror is adapted to direct the incident ray onto a surface of interest, and to collect back scattered light from said surface.

In some embodiments, the 3-D free space micromirror may have a diameter that ranges, but is not limited to, between about 50 micrometers to about 1000 micrometers and the hollow body is approximately, but not limited to, about 1 to about 100 millimeters in length and less then about 10 millimeter in diameter or width. However, other diameters and lengths of the hollow body are also contemplated.

The beam directing device, as used in the present invention may be a beam splitter, a fiber optic coupler, a beam coupler or other kind of device capable of splitting or combining a radiation ray. In the microprobe, the beam director may function as a beam splitter. The term 'beam splitter' is used herein in its conventional meaning that is an optical device that splits a beam of light into two. Examples of beam splitters include, but are not limited to, prisms, half-silvered mirrors, which are typically used in interferometers. Accordingly, the beam splitter is used in the microprobe to direct at least a part of the incident ray into the aperture and at least a part of the reflected ray to the image processing and visualization device. The term 'fiber optic coupler' is also used in its conventional meaning. In this regard, it refers to a mechanical component that interconnects a number of fiber optic cables in a bidirectional system by mixing and splitting all light signals within the cable. Accordingly, the fiber optic coupler is also used in the microprobe to direct at least a part of the incident ray into the aperture and at least a part of the reflected ray to the image processing and visualization device. Likewise, the term 'beam coupler' refers to a device that is capable of combining two or more radiation beams (or light beams) into a single beam.

In a further exemplary embodiment, the microprobe includes a hollow body closed at one end and having an aperture at an opposite end, at least one 3-D free space micromirror, at least one GRIN lens, at least two focusing lens, and a beam splitter.

Also in this exemplary embodiment, the beam splitter of the microprobe is arranged at the aperture end of the hollow body and is adapted to direct the incident light ray into the hollow body via the aperture. The arrangement of the at least two focusing lenses with respect to the aperture may be such that the distance between them is approximately twice the focal length of the first lens and the distance between the focusing lens and the GRIN lens may also be approximately twice the focal length of the second focusing lens. The micromirror may be arranged to have the GRIN lens focus directly on it or such that the micromirror directs the ray to be focused on the specific area of interest.

The microprobe disclosed here may also be integrated into a system for three-dimensional (3-D) bio-imaging. Such a system may include the microprobe described herein, a radiation source optically coupled to the microprobe, and an image processing and visualization device. The image processing and visualization device may be optically coupled to the microprobe such that the ray reflected by the micromirror is directed, via the aperture, to the image processing and visualization device by the focusing lens and beam director respectively.

In the above-mentioned system, any radiation source that produces rays suitable for generating an image may be used. Examples of such suitable radiation include rays found in the visible light spectrum, the infrared spectrum and the ultraviolet spectrum. As an example, a source that produces an incident ray in the infra-red spectrum having a wavelength between the visible spectrum, which starts at about 400 nm, to the far infrared spectrum of about 5 mm would be generally considered suitable. In one exemplary embodiment, the source may produce rays having a wavelength between about 700 nm-1 mm.

In the imaging system, any suitable image processing and visualization device may be used. The microprobe may be interfaced with various optical imaging devices and various techniques may be employed to obtain the required images. Examples of such devices include, but are not limited to, charge coupled devices (CCD) and photodiodes while the various techniques include, but are not limited to, optical coherent tomography, fluorescence spectroscopy and confocal scattering spectroscopy.

The microprobe capable of using an incident and reflected light ray for three-dimensional (3-D) bio-imaging, as is described herein, may be fabricated by the following method of fabricating:

(a) Providing a first substrate.
(b) Micro machining grooves on the surface of the first substrate for at least one focusing lens and at least one 3-D free space micromirror.
(c) Affixing the at least one focusing lens and micromirror in the respective grooves of the first substrate.
(d) Providing a second substrate.
(e) Micro machining an aperture and corresponding grooves on the surface of the second substrate to accommodate the affixed at least one focusing lens and a 3-D free space micromirror.
(f) Bonding the first and second substrates together to form the microprobe such that a hollow body closed at one end and having the aperture at an opposite end is enclosed within the first and second substrate.

The microprobe may be used for the analysis of a biological sample. Accordingly, a method of creating a three-dimensional (3-D) image of such a biological sample is described briefly. The said method generally includes the steps of (a) Inserting a microprobe into a biological sample to be analyzed,
(b) Providing a radiation source, which is capable of emitting a radiation ray,
(c) Introducing the radiation ray emitted by the radiation source into the probe, and
(d) Processing the outgoing ray to generate an image.

In the above method of use, the biological sample may be a part of a body of an animal, for example. Specifically, the biological sample may be selected from the group consisting of dental tissue, bone tissue, neural tissue, cardiovascular tissue and circulatory tissue. The bone tissue may be selected from a group consisting of, but not limited to, is a chord (e.g. a spinal chord), a finger bone, a femur or any other bone in the body.

Apart from functioning as a bio-imaging device, the present invention may also function as a therapeutic device. For example, in laser surgery, if the appropriate radiation source of the required intensity is used the microprobe may serve as the means for surgeons to access regions, especially in neurological and orthopedic surgical procedures where particular regions are presently inaccessible by conventional instruments. Accordingly, the microprobe may be used as a minimally invasive surgery (MIS) device. An additional use of the microprobe may be for root canal surgery, for example. In this regard, as the microprobe is thin is size, it may be inserted into the affected tooth to obtain an image of the canal of the tooth.

Further to the above-mentioned method of processing the outgoing ray, the outgoing ray may also be processed using an Optical Coherent Topography (OCT) method for imaging. The (OCT) method for imaging may be carried out in vivo or ex vivo. It should also be noted that it may be possible to process the outgoing ray of the probe for use in optical biopsy applications by in vivo or ex vivo methods.

DETAILED DESCRIPTION OF EXEMPLARY EMBODIMENTS

The following description serves to further illustrate the invention, and its various embodiments, and to aid in the understanding of the invention. However, it should be noted that the scope of the invention is by no means limited to only the various embodiments described hereafter.

Figure 1:
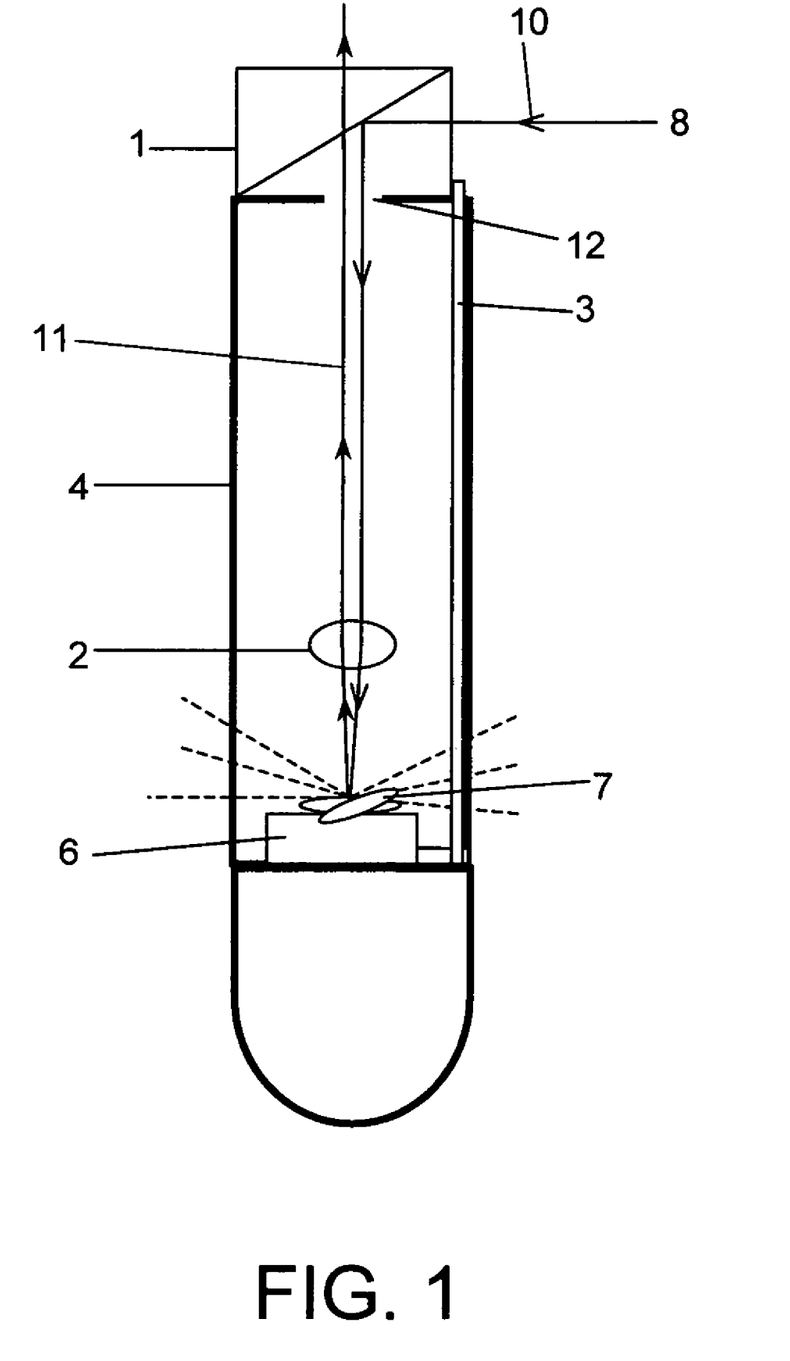
FIG. 1 illustrates a first embodiment of a microprobe having a single focusing lens.

FIG. 1 illustrates a first embodiment of a microprobe having a single focusing lens 2. The focusing lens 2 is placed within a hollow body 4. The hollow body 4 includes an aperture 12 at one end and is closed at its other end. A 3-D free space micromirror 7 is mounted on a substrate 6 and arranged at the focal distance of the focusing lens 2. The dashed lines around the 3-D micromirror indicate the various planes in which the micromirror may rotate and/or translate to. The movement of the 3-D micromirror is controlled using on or off chip control electronics, which is accessible by electrical line connection 3 situated along the edge of the hollow body 4. The electrical line connection 3 is attached to an external control electronics unit (not shown). The electronics control unit controls the current and/or voltages to achieve the desired deflection and orientation of the 3-D micromirror. The control unit may have a feedback loop to correct the orientation if required.

An incoming ray 10 from a radiation source 8 (not shown) enters the hollow body 4 by means of a beam director 1. The beam director 1 is arranged over the aperture 12 of the hollow body 4 such that the beam director 1 directs the incoming ray 10 into the hollow body. 4 via the aperture 12. The incoming ray 10 is incident on the focusing lens 2 and as the 3-D micromirror 7 lies at the focal length of the focusing lens 2, the ray 10 is correspondingly focused on said 3-D micromirror 7.

The incoming ray 10, now focused on the 3-D micromirror 7, is reflected by said mirror 7 and therefore gives rise to a reflected ray 11. The reflected ray 11 follows a substantially similar path as the incoming ray 10. The reflected ray 11 is incident on he focusing lens 2 and is directed through the aperture 12 and into the beam director 1. The beam director 1 directs the outgoing reflected ray 11 into a charged coupled device (CCD) 9 (not shown) to produce an image for viewing.

Figure 2:
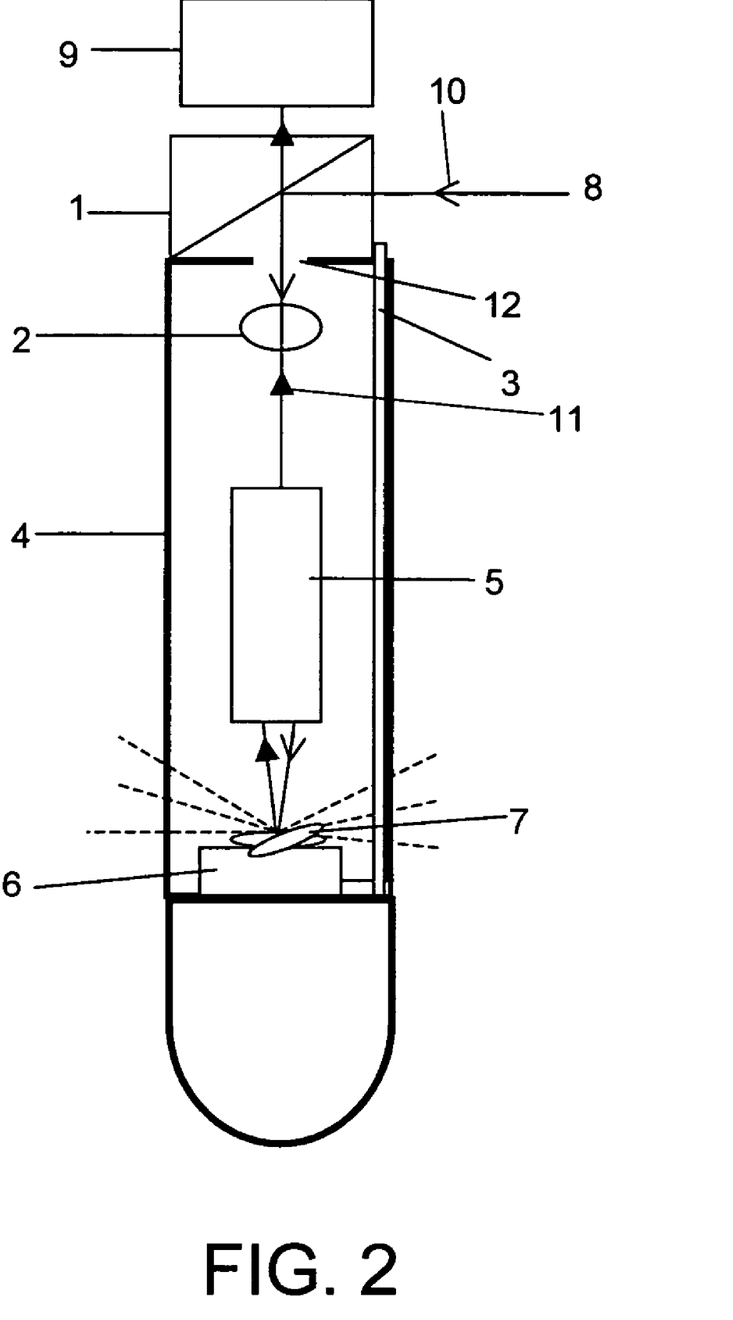
FIG. 2 illustrates a second embodiment of a microprobe having a focusing lens and a GRIN lens.

FIG. 2 illustrates a second embodiment of a microprobe having a focusing lens 2 and a GRIN lens 5. Essentially, the arrangement of all the other components, as described in FIG. 1, remain the same with the exception of the inclusion of the GRIN lens 5. The beam director 1 directs the incoming ray 10 into the hollow body 4, via the aperture 12. The incoming ray 10 is incident on the focusing lens 2 and is directed along towards the GRIN lens 5. The GRIN lens 5, having a varying refractive index, focuses the incoming ray 10 onto the 3-D micromirror 7, which in this embodiment, is arranged at the focal length of the GRIN lens 5.

The outgoing (or reflected) ray 11, as mentioned above, essentially follows the path of the incoming ray 10. Accordingly, the GRIN lens 5 directs the outgoing ray 11 to the focusing lens 2 and thereafter, to the beam director 1 via the aperture 12. The beam director 1 further directs the outgoing ray 11 to the CCD 9, which provides a visual image to a user.

Figure 3A:
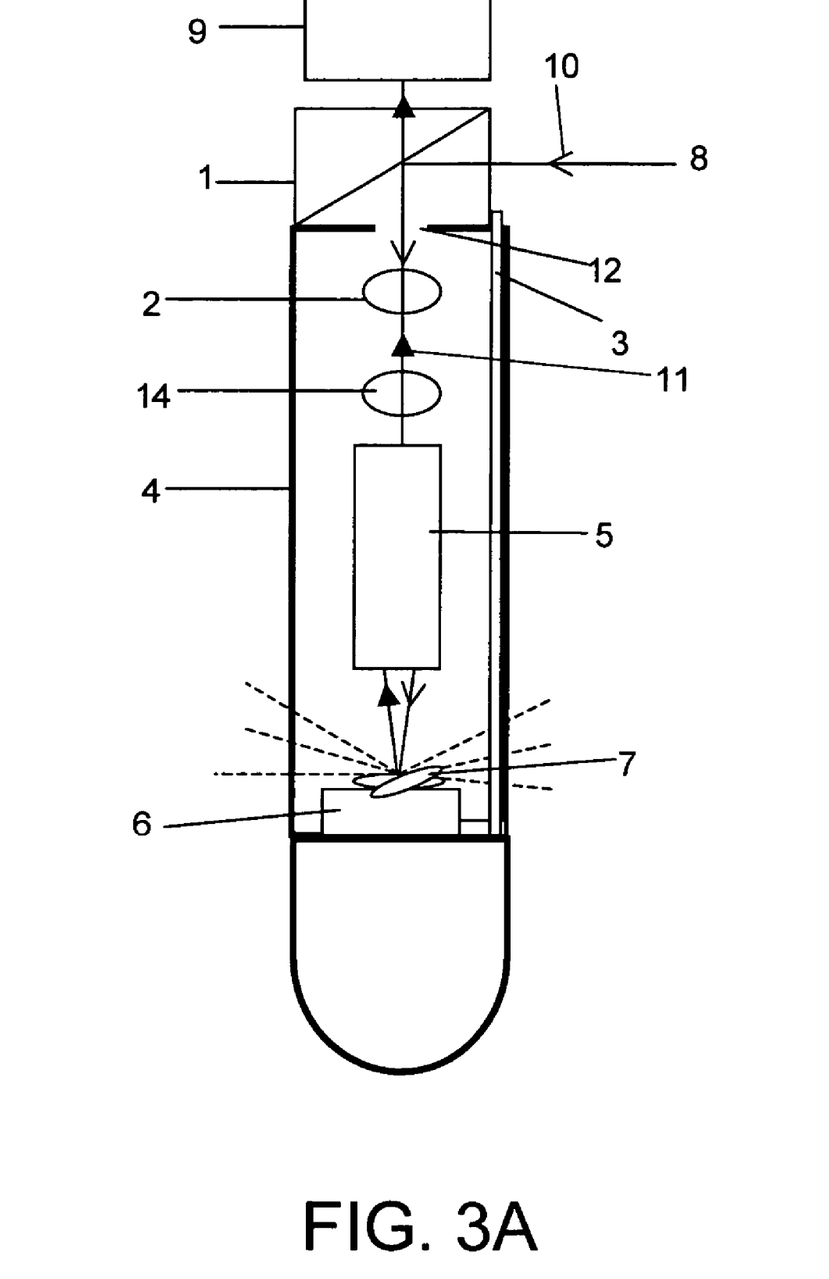
FIG. 3A illustrates a third embodiment of a microprobe having two focusing lenses and a GRIN lens.

FIG. 3A illustrates a third embodiment of a microprobe having two focusing lenses, 2 and 14, and a GRIN lens 5. The second focusing lens 14 is located in-between the first focusing lens 2 and the GRIN lens 5 of the embodiment of FIG. 2. The second focusing lens 14 enables the respective incoming and outgoing rays, 10 and 11, to be additionally focused thereby improving the image quality as later seen on the CCD 9.

Figure 3B:
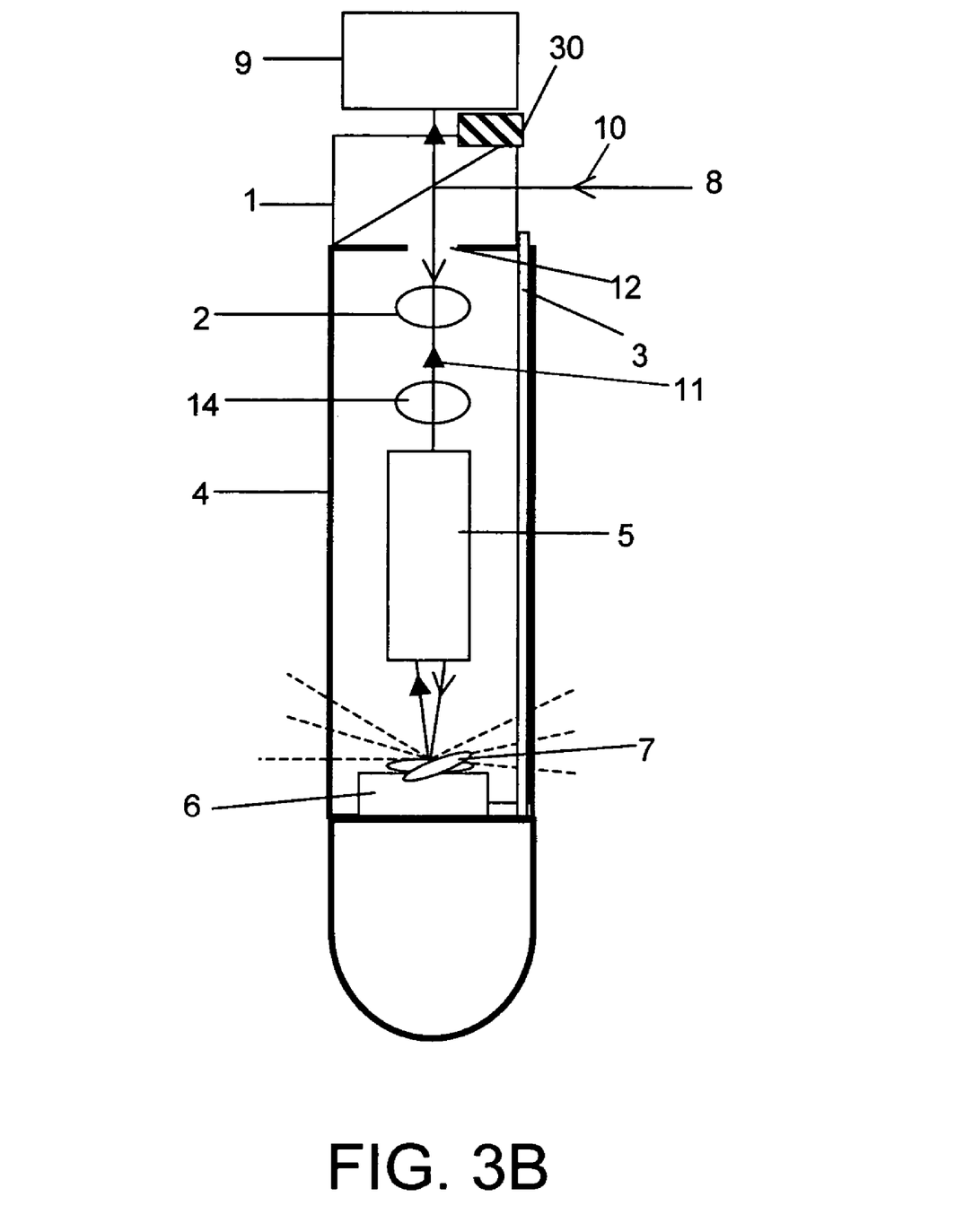
FIG. 3B illustrates a fourth embodiment of a microprobe having radio frequency (RF) communication device.

FIG. 3B illustrates a fourth embodiment of a microprobe. Essentially, the structure of the microprobe of FIG. 3B is the same as that of FIG. 3A, except that the microprobe of FIG. 3B includes a RF unit 30. The RF unit is located proximate to the aperture 12 of the hollow body 4. The RF unit 30 may be capable of functioning as a receiver, a transmitter or as a transceiver for the microprobe.

Figure 4:
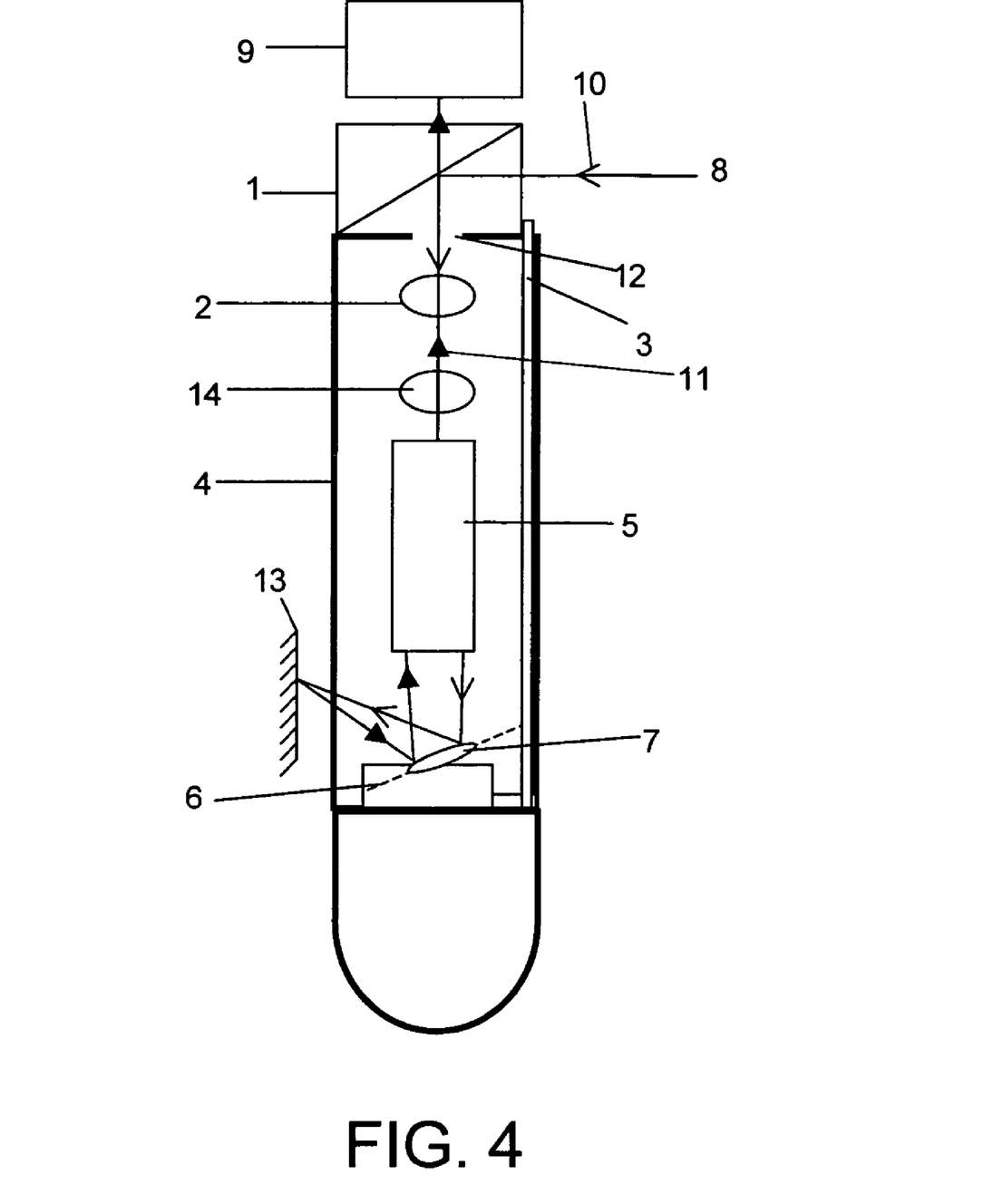
FIG. 4 illustrates an embodiment of a microprobe, wherein the focal point of the rays is external to the microprobe.

FIG. 4 illustrates an embodiment of a microprobe wherein the focal point of the rays 10 and 11 is external to the microprobe. In other words, in this embodiment, the incoming ray 10 and the outgoing ray 11 are not focused on the 3-D micromirror 7. Instead, the micromirror reflects the incoming ray such that it is focused on an area of interest 13 that lies outside the hollow body 4. Essentially, the 3-D micromirror 7 functions in the same way as in the previous embodiments. However, the positioning of said micromirror 7 is no longer at the focal point of the focusing lens 2 (or 14) or GRIN lens 5 as the case may be. Instead, the micromirror 7 is arranged at a distance such that the reflected ray incoming ray 10 is focused at a point on the area of interest 13.

In order to achieve the above-mentioned effect, the micromirror, being angularly orientatable, is actuated to direct and receive the incoming and outgoing rays accordingly. Also, the material of which the hollow body 4 is fabricated from allows for the rays to pass through without any hindrance. In the embodiments described herein, the material used may either be Silicon (Si) or glass. However, it should be noted that other materials, which permit the above-mentioned effect of having a ray focused outside of the hollow body 4, may also be used.

Figure 5:
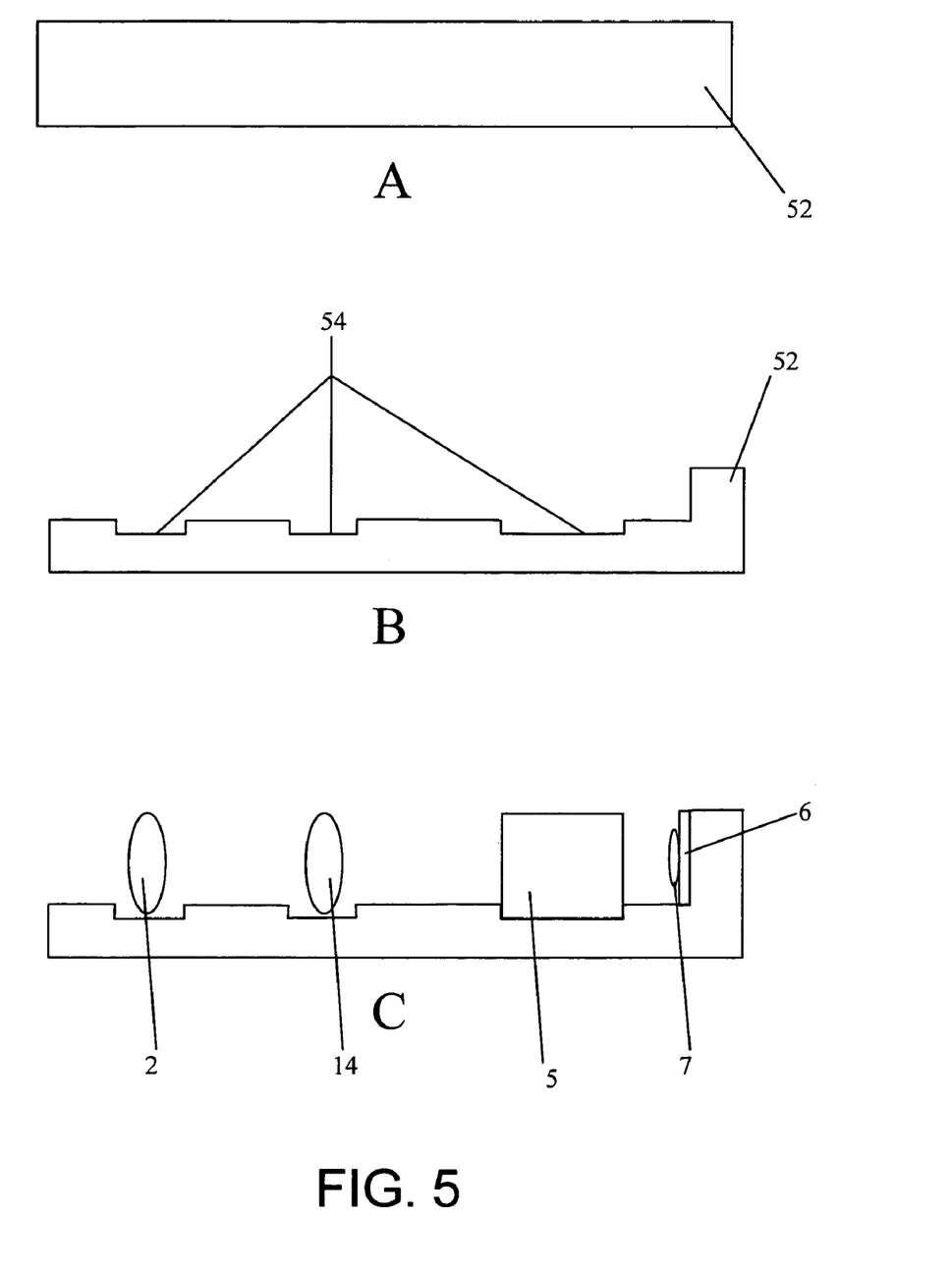
FIGS. 5A-5C illustrate the fabrication of a bottom patterned substrate that forms part of a hollow body of a microprobe.

FIGS. 5A-5C illustrate the fabrication of a bottom patterned substrate 52 that forms part of a hollow body of a microprobe. FIG. 5A simply shows a Si or glass substrate prior to any processing. In FIG. 5B, grooves 54 are micro machined onto the substrate 52 to give the resulting shape to the substrate. Subsequently in FIG. 5C, for the embodiment illustrated in FIG. 3 for example, two focusing lenses, 2 and 14 are placed in grooves 54 and the GRIN lens 5 is placed in another corresponding groove 54. The 3-D micromirror 7, mounted on a substrate 6 is bonded onto the patterned substrate 52 by means of high precision bonding according to the arrangement shown.

Figure 6:
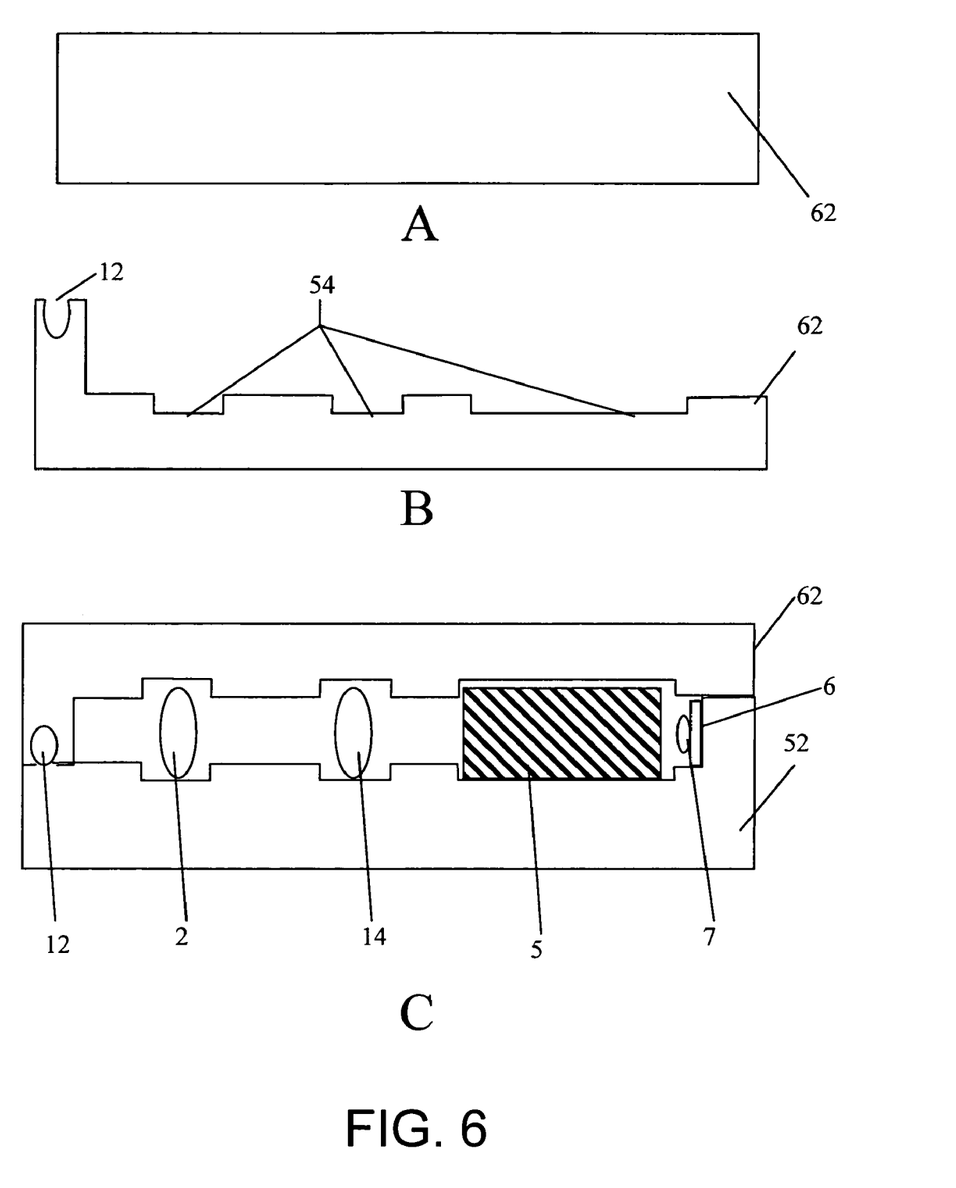
FIGS. 6A-6C illustrate the fabrication of a top patterned substrate that forms part of a hollow body of a microprobe.

FIGS. 6A-6C illustrate the fabrication of a top patterned substrate 62 that forms part of a hollow body of the microprobe. FIG. 6A simply shows a Si or glass substrate prior to any processing. In FIG. 6B, grooves 64 and an additional curved section for the aperture 12 are micro machined onto the substrate 62 to give the resulting shape to the substrate. FIG. 6C shows the assembly of the entire microprobe wherein the top substrate is bonded to the bottom substrate such that the interface between the top and bottom substrate is sealed to prevent any optical losses.

Figure 7:
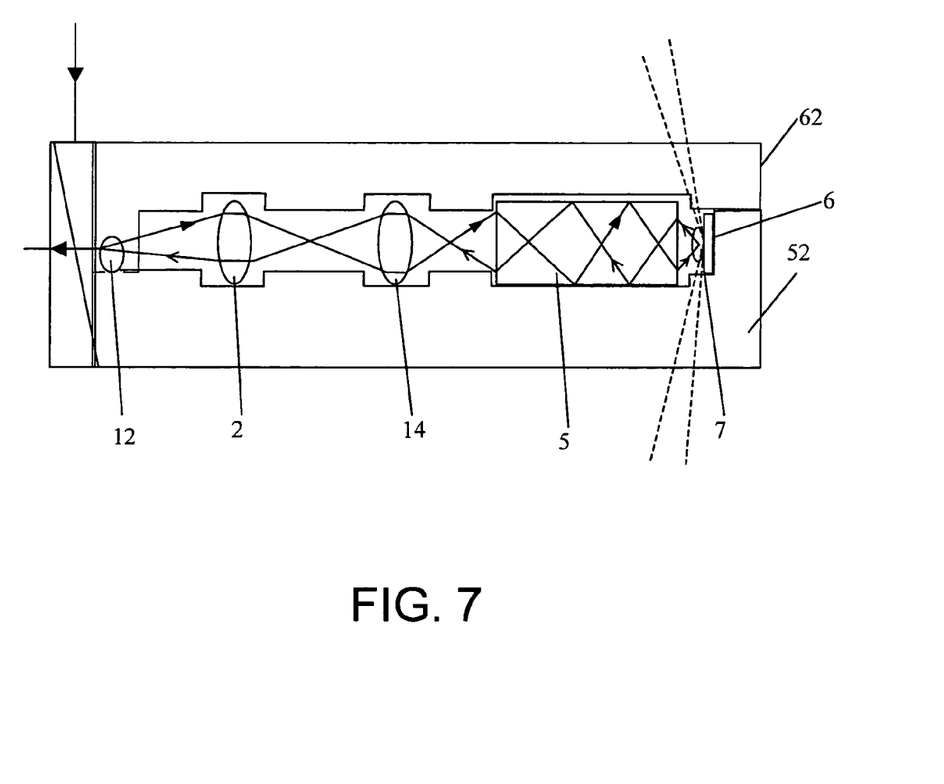
FIG. 7 shows the path of a ray in the embodiment of FIG. 3A.

FIG. 7 shows the path of a ray in the embodiment of FIG. 3A. As described earlier, the incoming ray 10 is directed through the aperture 12 and through two focusing lenses, 2 and 14 respectively. The distance between the focusing lenses 2 and 14 is approximately equivalent to twice the distance of the focal length of the first focusing lens 2. The distance between the second focusing lens 14 and the GRIN lens 5 is also approximately twice the focal length of the second focusing lens 14. Subsequently, in this particular embodiment, the 3-D micromirror 7 is placed at a distance from the GRIN lens 5 that allows the GRIN lens 5 to focus the ray at the micromirror 7.

Figure 8:
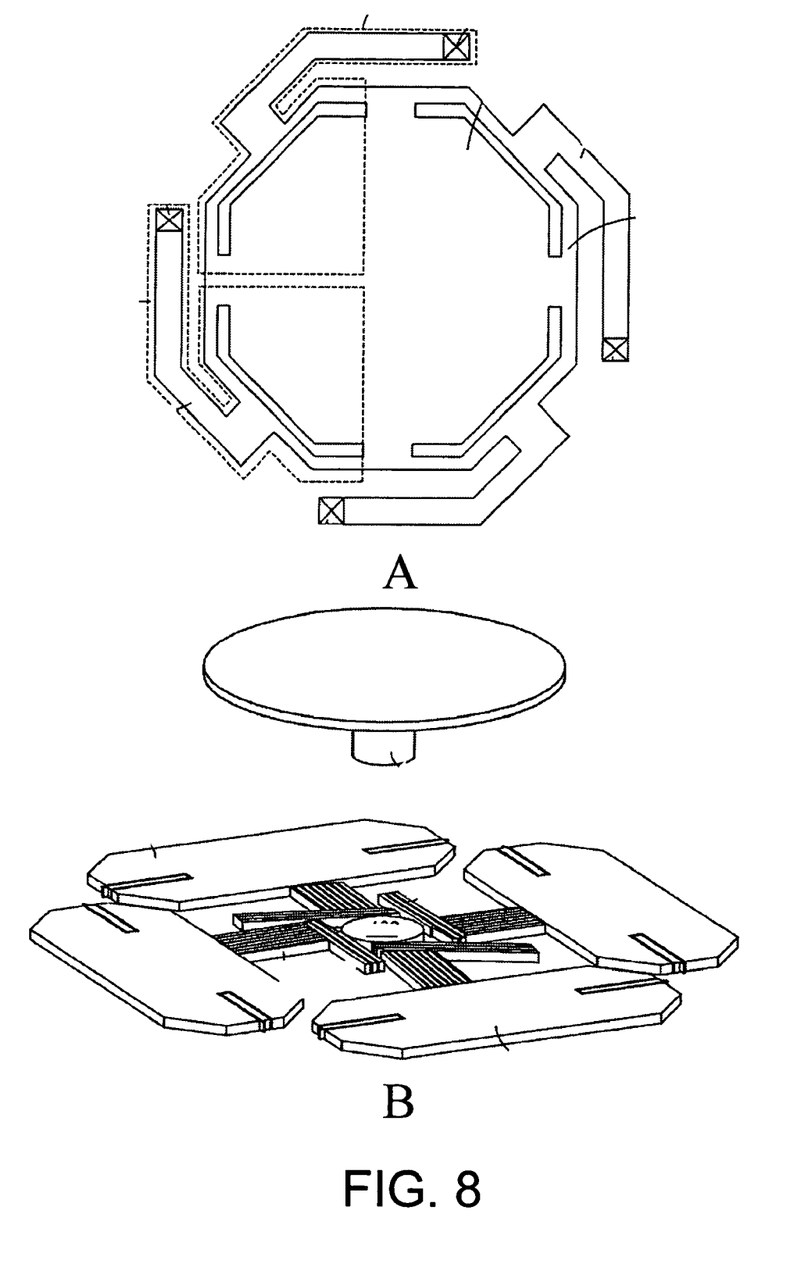
FIGS. 8A and 8B shows alternative 3-D micromirrors that may be used in embodiments of the microprobe.

FIGS. 8A and 8B show examples of further 3-D micromirrors that may be used in the present invention. Both the micromirrors shown here may be used in place of the 3-D free space micromirror 7 shown in the previous embodiments of FIGS. 1, 2, 3A, 3B and 4. Further examples of 3-D micromirrors that may be used are discussed in detail in U.S. Pat. Nos. 6,563,106, 6,556,737, 6,480,320, 6,504,643 and 6,386,716, for example. It should be noted that the 3-D micromirrors used in connection with the present invention are not limited to those mentioned or illustrated alone.

Figure 9:
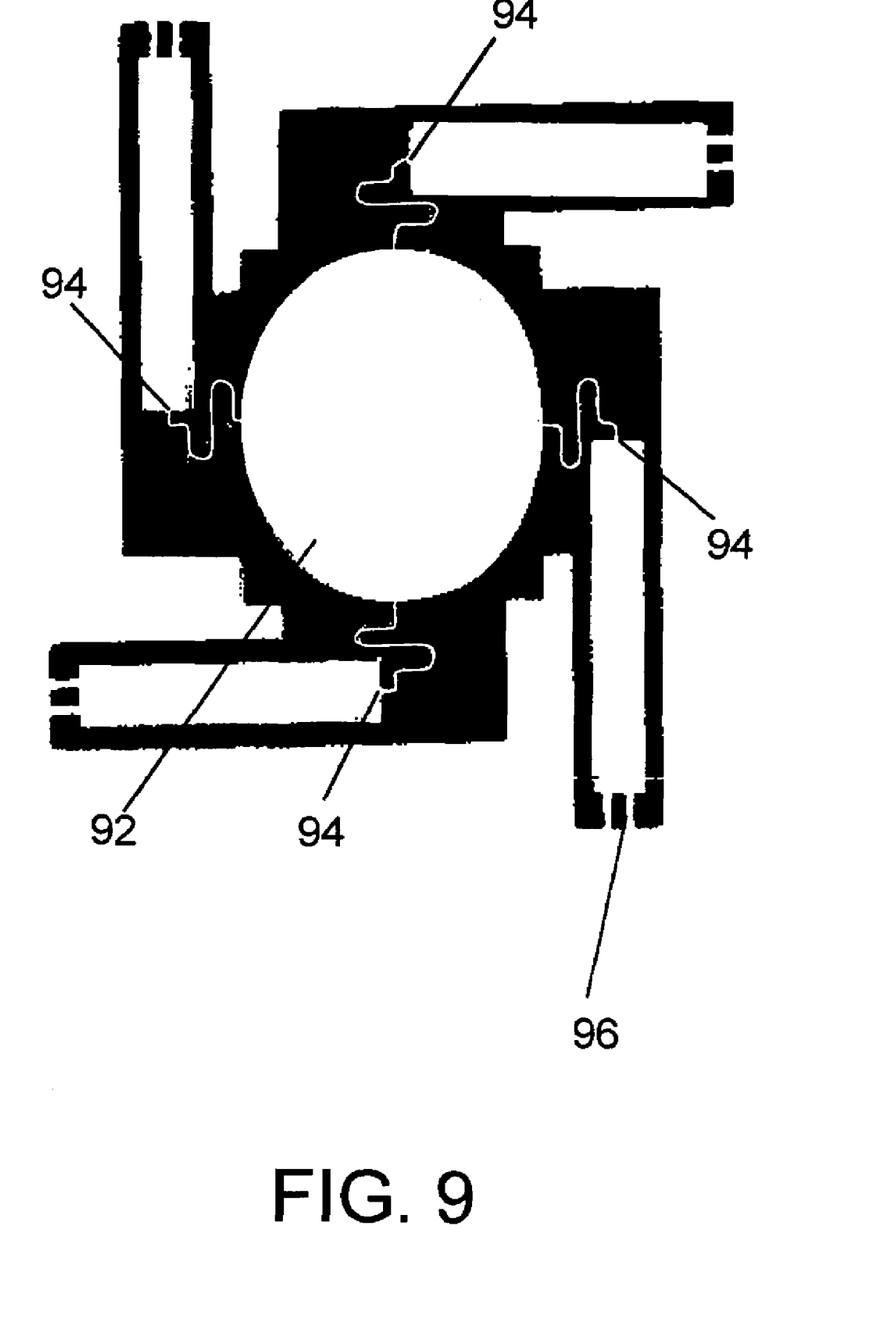
FIG. 9 illustrates a 3-D free space micromirror that is used in a microprobe.

FIG. 9 illustrates the 3-D free space micromirror 7 that is used in the present invention. The micromirror 7 has a crystal silicon mirror 92, which is connected with four crystal silicon actuators 94. The control over the crystal silicon actuators 94 is provided for by the electrical connections 96 that are found in connection with the respective crystal silicon actuators 94. The electrical connections allow the current and/or voltage to be regulated and varied to the actuators 94 so as to provide the required 3-D motion to the crystal silicon micromirror. As mentioned above, the actuators may also be controlled by thermal, electrostatic and piezoelectric means.

Figure 10:
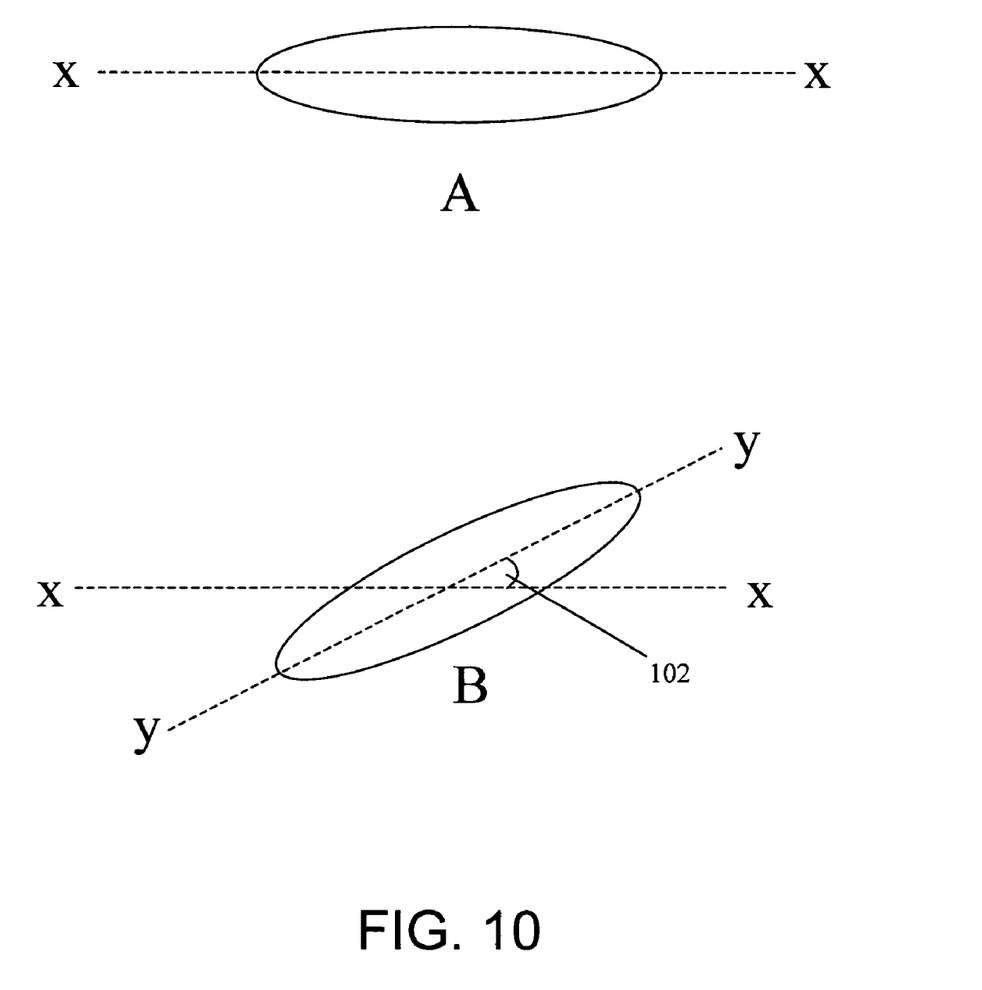
FIG. 10A illustrates a default position of a 3-D micromirror with respect to the horizontal line x-x and FIG. 10B illustrates a 3-D micromirror that lies in the plane y-y, at an angle to the horizontal plane x-x.

FIG. 10A illustrates a default position of the 3-D micromirror 7 with respect to the horizontal line x-x and FIG. 10B illustrates a 3-D micromirror 7 that lies in the plane y-y, at an angle to the horizontal plane x-x. The micromirror 7 is shown to be at angle 102 to the horizontal axis x-x. In such an orientation, the micromirror 7 now lies in the plane y-y and accordingly, is able to direct and reflect the respective incoming and outgoing rays to and from a specific area. Accordingly, the micromirror may also be adapted to be orientatable in multiple planes in order to direct and receive rays from multiple areas (scanning) such that in combination, said scanning results in providing a 3-D image of the various areas of interest in a biological sample, for example. As an example, the 3-D micromirror may be able to rotate between a plane of about ±60 degrees from the radial axis of the hollow body of the microprobe.

Figure 11:
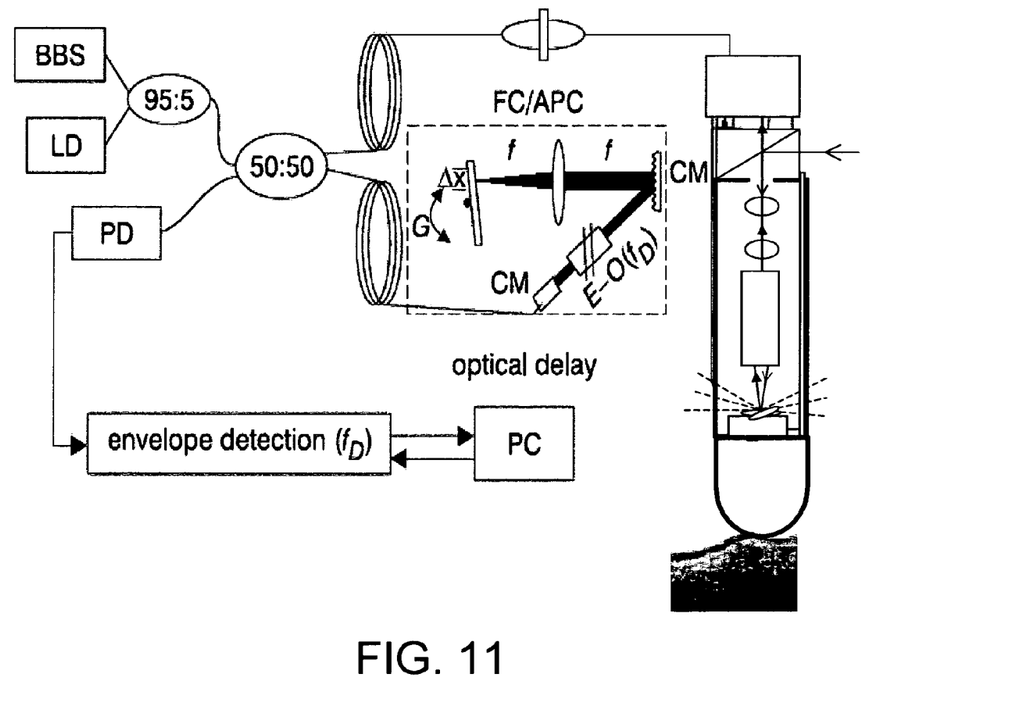
FIG. 11 illustrates the use of a microprobe for Optical Coherent Tomography (OCT) applications.

FIG. 11 illustrates the use of a microprobe in OCT. OCT may be considered to be analogous to ultrasound or radar, but measures reflected infrared rays instead. The resolution of the image obtained may be as small as 2um provide a depth penetration of between 2-3 mm of the tissue. Accordingly, it may be considered to have the resolution comparable to that at the cellular level and may therefore be used to provide an 'Optical Biopsy'. The 'Optical Biopsy' is non-invasive or minimally invasive using present endoscopic probes and even less so in the case of the present microprobe. Accordingly, the removal of a tissue specimen is not required.

Further potential applications are early stage cancer detection, diagnosis of cartilage injury and repair, and assessment of tissue growth as the high spatial resolution offered by the optical method provides the microprobe with the ability to detect small tumors.

The following experimental examples serve to illustrate the use for the above-mentioned device in some of the mentioned applications such as neural tissue and dental tissue bio-imaging, for example.

EXAMPLES

Example 1

Optical Coherence Tomography

The probe can be attached to other systems such as OCT (Optical coherent tomography) for in vivo or ex vivo imaging of tissues or cancer cells or other type of body cells The probe can be used as a beam delivery unit in a OCT setup. In this case a fiber optic coupler is used to split the beam equally (sample and reference). (See FIG. 1). One beam is used in the probe and another beam is as a reference beam. OCT generate images by measuring the echo delay time of light using low coherence interferometry. The light backscattered from the object being imaged is correlated with the light that travels a known reference path.

The above illustrations, accompanying description and examples of use of the various embodiments of the present invention merely serve to aid in the understanding principle of the said invention. Accordingly, it should not be construed that the present invention described herein is simply limited to the illustrated embodiments of the device and/or apparatus.

What is claimed is:

1. A microprobe that is capable of using an incident and reflected radiation ray for three-dimensional (3-D) bio-imaging, said microprobe comprising:
    a hollow body closed at one end and having an aperture at an opposite end;
    a 3-D free space micromirror;
    a first focusing lens and second focusing lens;
    a gradient index (GRIN) lens;
    a beam director;
    wherein the beam director is arranged at the aperture end of the hollow body and is adapted to direct at least a part of the incident ray into the hollow body via the aperture;
    wherein within said hollow body is the first focusing lens and the micromirror arranged respectively from the aperture, such that the distance between the first focusing lens and the micromirror allows for the incident ray to be directed onto the micromirror; and
    wherein the GRIN lens is arranged between the second focusing lens and the micromirror and wherein the GRIN lens allows for the incident ray to be directed onto the micromirror.

2. The microprobe of claim 1, further comprising an RF device, wherein said RF unit is selected from the group consisting of a transmitter, a receiver or a transceiver device.

3. The microprobe of claim 2, wherein the hollow body comprises at least two patterned substrates bonded together.

4. The microprobe of claim 3, wherein the patterned substrates have an inner surface with grooves formed thereon.

5. The microprobe of claim 4, wherein the grooves on the inner surface of the hollow body have the focusing lens, the GRIN lens, or any combination thereof, and the micromirror affixed therein and arranged respectively from the aperture.

6. The microprobe of claim 5, wherein the 3-D free space micromirror comprises:
    a crystal silicon micromirror;
    a crystal silicon actuator; and
    a crystal silicon flexible spring connecting said crystal silicon actuator to said crystal silicon micromirror.

7. The microprobe according to claim 6, wherein the actuation of the one silicon actuator is carried out by a means selected from the group consisting of thermal variation, electrostatic charging and piezoelectric transduction.

8. The microprobe according to claim 6, wherein the 3-D free space micromirror comprises four silicon actuators.

9. The microprobe according to claim 6, wherein the 3-D free space micromirror is adapted to direct and collect light rays in at least one plane, wherein the at least one plane is tilted to the radial axis of the probe.

10. The microprobe according to claim 6, wherein the 3-D free space micromirror is adapted to direct the incident ray onto a surface and to collect back scattered light from said surface about the radial axis or the vertical axis of the microprobe.

11. The microprobe according to claim 6, wherein the 3-D free space micromirror has a diameter that ranges between about 50 micrometers to about 1000 micrometers.

12. The microprobe according to claim 6, wherein the micromirror is affixed to the grooves of the hollow body by high precision bonding means.

13. The microprobe of claim 3, wherein the two patterned substrates having grooves thereon are made from silicon (Si) or glass.

* * * * *

UNITED STATES PATENT AND TRADEMARK OFFICE
CERTIFICATE OF CORRECTION

| | | |
|---|---|---|
| PATENT NO. | : 7,616,987 B2 | Page 1 of 1 |
| APPLICATION NO. | : 11/244919 | |
| DATED | : November 10, 2009 | |
| INVENTOR(S) | : Premachandran et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 672 days.

Signed and Sealed this

Nineteenth Day of October, 2010

David J. Kappos
*Director of the United States Patent and Trademark Office*